United States Patent [19]

Langlois

[11] Patent Number: 4,816,596
[45] Date of Patent: * Mar. 28, 1989

[54] PROCESS FOR PREPARING TRIFLUOROETHOXYBENZENE OR TRIFLUOROETHYLTHIOBENZENE

[75] Inventor: Bernard Langlois, Lyon, France
[73] Assignee: Rhone-Polenc Specialites Chimoues, Courbevoie, France
[*] Notice: The portion of the term of this patent subsequent to Feb. 1, 2006 has been disclaimed.
[21] Appl. No.: 845,586
[22] Filed: Mar. 28, 1986

[30] Foreign Application Priority Data

Mar. 29, 1985 [FR] France ................. 85 04758

[51] Int. Cl.$^4$ .................. C07C 121/52; C07C 121/62
[52] U.S. Cl. ..................... 358/423; 558/425; 560/10; 560/18; 560/56; 560/65; 568/43; 568/44; 568/52; 568/54; 568/56; 568/328; 568/333; 568/588; 568/633; 568/637; 568/649; 568/655; 568/656
[58] Field of Search ............... 568/655, 333, 588, 633, 568/52, 44, 43, 54, 56, 656, 637, 649, 328; 558/423, 425; 560/18, 10, 56, 65

[56] References Cited

U.S. PATENT DOCUMENTS 3,419,595 12/1968 Hansen .................. 568/56
4,287,125 1/1981 Soula ..................... 568/56
4,643,811 2/1987 Langlois .................. 204/157.8

FOREIGN PATENT DOCUMENTS 2529543 9/1982 France .
2045760A 6/1980 United Kingdom .

OTHER PUBLICATIONS

Camps et al., "A Simple Method for Preparation of Aryl, 2,2,2-Trifluoroethyl Ethers", Synthesis No. 9, pp. 727-728 (980).

Nakai et al., "A Convenient Preparation of Arylthioynamines", Bulletin of the Chemical Society of Japan, vol. 50, No. 11, pp. 3069-3070 (1977).

W. P. Weber et al, Phase Transfer Catalysis in Organic Synthesis, pp. 1-15, Springer-Verlag, New York (1977).

Primary Examiner—Mary E. Ceperley
Attorney, Agent, or Firm—Finnegan, Henderson, Farabow, Garrett, & Dunner

[57] ABSTRACT

A process for preparing substituted or unsubstituted trifluoroethoxy- or trifluoroethylthiobenzenes by reaction of a phenol or thiophenol, both of which may be substituted or unsubstituted, with a compound of the formula $CF_3—CH_2—O—R'$, where R' is a moiety selected from the group consisting of trifluoroacetyl, methanesulfonyl, paratoluenesulfonyl, trichloromethanesulfonyl and chlorosulfonyl, in the presence of a strong alkaline base and a complexing agent of the formula:

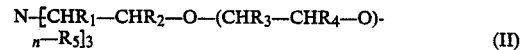

wherein n is an integer from 0 to 10 (0 is less than or equal to n is less than or equal to 10), $R_1$, $R_2$, $R_3$ and $R_4$, which may be identical or different, are selected from the group consisting of a hydrogen atom and an alkyl moiety having from 1 to 4 carbon atoms, and $R_5$ denotes an alkyl or cycloalkyl moiety having from 1 to 12 carbon atoms, a phenyl moiety or a moiety of the formula: $—C_mH_{2m}—C_6H_5$ or $C_mH_{(2m+1)}—C_6H_4—$, where m is from 1 to 12.

22 Claims, No Drawings

PROCESS FOR PREPARING TRIFLUOROETHOXYBENZENE OR TRIFLUOROETHYLTHIOBENZENE

The present invention relates to a process for preparing substituted or unsubstituted trifluoroethoxy- or trifluoroethylthiobenzenes.

It is known from French Patent No. 2,468,576 to prepare trifluoroethoxybenzene derivatives by reaction of a phenol with 2,2,2-trifluoroethyl trifluoromethanesulfonate or by reaction of dibromobenzene with trifluoroethanol in the presence of sodium hydride and a copper-containing catalyst.

The first process possesses the disadvantage of using as a starting material 2,2,2-trifluoroethyl trifluoromethanesulfonate, which is not commercially available in large quantities. At the industrial level this lack of availability imposes an irremediable burden on the cost of obtaining trifluoroethoxy benzene.

The second process disadvantageously possesses poor industrial reproducibility in some cases and also requires the use of a costly aprotic solvent, the recycling of which is difficult. These disadvantages limit the industrial usefulness of the second process.

It is also known from Synthesis 1980 (9), 727–8 to prepare 2,2,2-trifluoroaryl ethers by condensation of a phenol with 2,2,2-trifluoroethyl methanesulfonate in the presence of a strong base in hexamethylphosphorotriamide. The latter solvent, however, cannot be used in industry on account of its toxicity.

None of the processes previously described enables trifluoroethoxybenzenes or trifluoroethylthiobenzenes to be obtained at a cost which permits industrial exploitation to be envisaged.

The present invention can overcome the disadvantages of the prior art. The present invention relates to a process for preparing substituted or unsubstituted trifluoroethoxy- or trifluoroethylthiobenzenes, wherein a substituted or unsubstituted phenol or a substituted or unsubstituted thiophenol is reacted with a compound of formula (I):

$$CF_3-CH_2-O-R' \quad (I)$$

wherein R' is a moiety selected from the group consisting of trifluoroacetyl, methanesulfonyl, paratoluenesulfonyl, trichloromethanesulfonyl and chlorosulfonyl, in the presence of a solid strong alkaline base and at least one complexing agent of the formula:

wherein n is an integer ranging from 0 to 10 (0 is less than or equal to n is less than or equal to 10), $R_1$, $R_2$, $R_3$ and $R_4$, which may be identical or different, are selected from the group consisting of a hydrogen atom and an alkyl moiety having from 1 to 4 carbon atoms, and $R_5$ is selected from the group consisting of an alkyl moiety having from 1 to 12 carbon atoms, a cycloalkyl moiety having from 1 to 12 carbon atoms, a phenyl moiety and a moiety of the formula: $-C_mH_{2m}C_6H_5$ or $C_mH_{2m+1}C_6H_4-$, m ranging from 1 to 12.

Preferably, the phenol or thiophenol used according to the invention is of the formula:

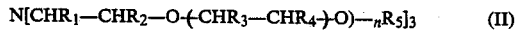

in which:
Ar is a monocyclic, polycyclic or heterocyclic aromatic ring system;
A is sulfur or oxygen;
R is at least one moiety selected from the group consisting of hydrogen, halogen, alkyl, preferably $C_1-C_6$ alkyl, alkoxy, preferably $C_1-C_6$ alkoxy, alkylthio, preferably $C_1-C_6$ alkylthio, phenoxy, nitro, haloalkyl, preferably $C_1-C_6$ haloalkyl, alkoxycarbonyl, preferably $C_1-C_6$ alkoxycarbonyl, haloalkoxy, preferably $C_1-C_6$ haloalkoxy, haloalkylthio, preferably $C_1-C_6$ haloalkylthio, phenyl, benzoyl, and cyano; and
n denotes an integer from 1 to 5.

It is particularly preferred to use phenols or thiophenols of formula (III) in which n is 1 or 2.

It is particularly preferred to use 2,2,2-trifluoroethyl para-toluenesulfonate and 2,2,2-trifluoroethyl trichloromethanesulfonate as the compound of formula (I).

It is more particularly preferred to use 2,2,2-trifluoroethyl para-toluenesulfonate.

The base employed in the process of the invention is preferably selected from the group consisting of alkali metal and alkaline earth metal hydroxides and carbonates. Examples of such compounds include sodium hydroxide, potassium hydroxide, sodium or potassium carbonate and lime.

According to a preferred embodiment of the invention, a complexing agent of formula (II) is used in which $R_1$, $R_2$, $R_3$ and $R_4$ denote a hydrogen atom or a methyl moiety, and $R_5$ and n have the meanings given above.

Among these compounds, it is more preferable to employ complexing agents for which n is greater than or equal to 0 and less than or equal to 6 and for which $R_5$ denotes an alkyl moiety having from 1 to 4 carbon atoms.

Preferred complexing agents include:
tris(3-oxabutyl)amine of the formula: $N-(CH_2-CH_2-O-CH_3)_3$;
tris(3,6-dioxaheptyl)amine of the formula: $N-(CH_2-CH_2-O-CH_2-CH_2-O-CH_3)_3$;
tris(3,6,9-trioxadecyl)amine of the formula: $N-(CH_2-CH_2-O-CH_2-CH_2-O-CH_2-CH_2-O-CH_3)_3$;
tris(3,6-dioxaoctyl)amine of the formula: $N-(CH_2-CH_2-O-CH_2-CH_2-O-C_2H_5)_3$;
tris(3,6,9-trioxaundecyl)amine of the formula: $N-(CH_2-CH_2-O-CH_2-CH_2-O-CH_2-CH_2-O-C_2H_5)_3$;
tris(3,6-dioxanonyl)amine of the formula: $N-(CH_2-CH_2-O-CH_2-CH_2-O-C_3H_7)_3$;
tris(3,6,9-trioxadodecyl)amine of the formula: $N-(CH_2-CH_2-O-CH_2-CH_2-O-CH_2-CH_2-O-C_3H_7)_3$;
tris(3,6-dioxadecyl)amine of the formula: $N-(CH_2-CH_2-O-CH_2-CH_2-O-C_4H_9)_3$;
tris(3,6,9-trioxatridecyl)amine of the formula: $N-(CH_2-CH_2-O-CH_2-CH_2-O-CH_2-CH_2-O-C_4H_9)_3$;
tris(3,6,9,12-tetraoxatridecyl)amine of the formula: $N[CH_2-CH_2-O(CH_2-CH_2-O)_3CH_3]_3$;
tris(3,6,9,12,15,18-hexaoxanonadecyl)amine of the formula: $N[CH_2-CH_2-O(CH_2-CH_2-O)_5CH_3]_3$;
tris(3,6-dioxa-4-methylheptyl)amine of the formula: $N(CH_2-CH_2-O-CH(CH_3)-CH_2-O-CH_3)_3$;
and
tris(3,6-dioxa-2,4-dimethylheptyl)amine of the formula: $N[CH_2-CH(CH_3)-O-CH(CH_3)CH_2-O-CH_3]_3$.

The amines used in the process according to the invention are known as such in the prior art. For example, French Patent No. 1,302,365 mentions the production of the tertiary amines N(CH$_2$—CH$_2$—O—CH$_3$)$_3$ and N—(CH$_2$—CH$_2$—O—CH$_2$—CH$_2$—O—CH$_3$)$_3$ as by-products of the synthesis of the corresponding primary and secondary amines.

According to a special embodiment of the invention, a solvent intermediary is used. The solvent has to satisfy certain conditions: it has to solubilize the complexing agent and be chemically inert with respect to the compounds to be dissolved. This solvent is preferably selected from low cost apolar or only slightly polar aprotic solvents such as, for example, chlorobenzene, ortho-dichlorobenzene, 1,2,4-trichlorobenzene or carbon tetrachloride. Trichlorobenzene is preferred.

If a solvent intermediary is not used, the phenol or thiophenol performs the role of solvent. A solvent is preferred when the phenol or thiophenol has an excessively high melting point or is excessively reactive.

The mole ratio of the phenol or thiophenol to the compound of formula (I) is preferably from about 0.5 to 5. A mole ratio from 0.7 to 1.5 is preferably used.

According to a special embodiment of the invention, the base is used in an amount such that the mole ratio of the base to the phenol or thiophenol is from about 0.5 to 1.1.

The mole ratio of the amine of formula (II) to the phenol or thiophenol, preferably of formula (III), is preferably from about 0.01 to 0.2.

The temperature to which the reaction medium is subjected is preferably from about 80° to 200° C.

The reaction is preferably carried out at atmospheric pressure, but a higher pressure is in no way excluded from the scope of the invention. One skilled in the art will select a pressure suitable for the economics of the process.

The isolation of the final products from the reaction mixture is carried out by filtration followed by distillation, without any ancillary treatment being applied, which is an advantage compared to the processes of the prior art.

Representative compounds obtained according to the process of the invention include: (2,2,2-trifluoroethoxy)benzene, chloro-, methyl-, methoxy-, nitro-, cyano-, trifluoromethyl- and fluoro-(2,2,2-trifluoroethoxy)benzenes, 2'-(2,2,2-trifluoroethoxy)naphthalene, (2,2,2-trifluoroethylthio)benzene and chloro- and nitro-(2,2,2-trifluoroethylthio)benzenes.

The (trifluoroethoxy)- or (trifluoroethylthio)benzenes of the present invention are used as synthesis intermediates for the preparation of derivatives having pharmaceutical, veterinary or phytosanitary activity, and in the lubricant industry (French Patent No. 2,468,576).

The invention will now be described more completely by means of the following examples, which in no way limit the invention.

SYNTHESIS OF 4-CHLORO-(2,2,2-TRIFLUOROETHOXY)BENZENE

A 500 ml round-bottomed flask equipped with a mechanical stirrer, a thermometer and a small Vigreux type distillation column is charged with the following:
200 ml of 1,2,4-trichlorobenzene;
4 g (0.1 mole) of finely ground sodium hydroxide;
1.6 g (5×10$^{-3}$ mole) of tris(3,6-dioxaheptyl)amine; and
12.9 g (0.1 mole) of para-chlorophenol.

This suspension was stirred and brought to 100° C., at which temperature the water began to distill. The medium was maintained at from 100° to 130° C. until the distillation of the water formed ceased.

The mixture was cooled to about 30° C. and 28.2 g (0.1 mol) of 2,2,2-trifluoroethyl trichloromethanesulfonate were introduced into the reaction mixture.

The distillation column was replaced with a reflux condenser, and the reaction medium was brought with stirring to 145° C., which temperature was maintained for 4 hours.

Gas chromatographic analysis with an internal standard indicated that there was a crude yield of 4-chloro-(2,2,2-trifluoroethoxy)benzene of 58%.

After being cooled, the mixture obtained was filtered and the filtrate was subjected to distillation under reduced pressure using a spinning band column.

11.6 g of 4-chloro-(2,2,2-trifluoroethoxy)benzene were thereby collected, representing a 55% yield. (B.p.$_{25}$ 77°–77.5° C.).

Examples 2–9 are summarized in the following table:

TABLE I

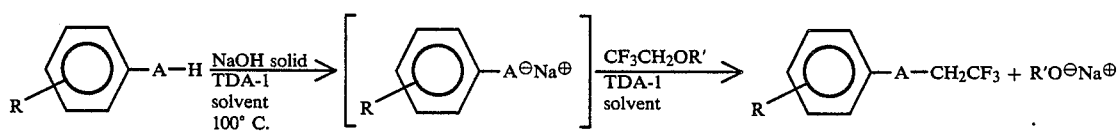

| Example | R | A | Solvent | R' | Ar—A—H CF$_3$CH$_2$OR' mole/mole | NaOH Ar—AH moles/moles | TDA-1 Ar—A—H (moles %) | [Ar—A—H] moles | T °C. | Time (h) | Yield Ar—A—CH$_2$CF$_3$ % |
|---|---|---|---|---|---|---|---|---|---|---|---|
| 2 | H | O | TCB | TsO | 1 | 1 | 5 | 0.4 | 170° C. | 6 | 31% crude 21% distilled |
| 3 | 4-CH$_3$ | O | TCB | CCl$_3$SO$_2$ | 0.7 | 1 | 4 | 0.5 | 145° C. | 4 | 59% distilled |
| 4 | 4-CH$_3$O | O | TCB | CH$_3$SO$_2$ | 1 | 1 | 5 | 0.33 | 140° C. | 6 | 21% crude |
| 5 | 2-Cl | O | TCB | CCl$_3$SO$_2$ | 1 | 1 | 5 | 0.5 | 145° C. | 4 | 61% distilled |
| 6 | 4-Cl | O | TCB | CCl$_3$SO$_2$ | 1.2 | 0.85 | 5 | 0.5 | 145° C. | 4 | 58% crude 55% distilled |
| 7 | 4-Cl | O | TCB | TsO | 1 | 1 | 5 | 0.5 | 150° C. + 186° C. + 186° C. | 6 6 2 | 27% crude 57% crude 70% crude |
| 8 | H | S | TCB | CF$_3$CO | 1 | 1 | 7.6 | 0.7 | 120–140° C. | 12 | 34% distilled |

TABLE I-continued

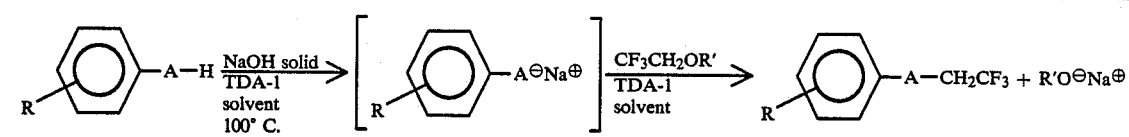

| Example | R | Solvent | A | R' | Ar—A—H / CF₃CH₂OR' mole/mole | NaOH / Ar—AH moles/moles | TDA-1 / Ar—A—H (moles %) | [Ar—A—H] moles | T °C. | Time (h) | Yield Ar—A—CH₂CF₃ % |
|---|---|---|---|---|---|---|---|---|---|---|---|
| 9 | 2-OH—C₁₀H₇ (III) | TCB | | TsO | 1 | 1 | 15 | 0.5 | 140° C. + 160° C. | 12 +6 | 20% crystallized |

TCB = 1,2,4-trichlorobenzene

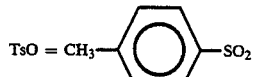
TsO = CH₃—⟨phenyl⟩—SO₂

TDA-1 = N(CH₂—CH₂—O—CH₂—CH₂—O—CH₃)₃

What is claimed is:

1. A process for preparing a substituted or an unsubstituted trifluoroethoxyarene or a substituted or an unsubstituted trifluoroethylthioarene comprising the step of reacting, for a time sufficient to obtain said trifluoroethoxyarene or trifluoroethylthioarene, a substituted or an unsubstituted arene containing an OH substituent or an SH substituent with a compound of the formula (I):

CF₃CH₂OR'     (I)

wherein R' is a moiety selected from the group consisting of trifluoroacetyl, methanesulfonyl, paratoluenesulfonyl, trichloromethanesulfonyl and chlorosulfonyl, in the presence of a solid strong alkaline base and at least one complexing agent of the formula (II):

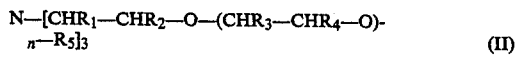
N—[CHR₁—CHR₂—O—(CHR₃—CHR₄—O)ₙ—R₅]₃     (II)

wherein n is an integer from 0 to 10 (0 is less than or equal to n is less than or equal to 10), R₁, R₂, R₃ and R₄, which may be identical or different, are selected from the group consisting of a hydrogen atom and an alkyl moiety having from 1 to 4 carbon atoms, and R₅ is selected from the group consisting of an alkyl moiety having from 1 to 12 carbon atoms, a cycloalkyl moiety having from 1 to 12 carbon atoms, a phenyl moiety and a moiety of the formula: —CₘH₂ₘ—C₆H₅ or CₘH₂ₘ₊₁—C₆H₄—, wherein m ranges from 1 to 12.

2. The process of claim 1, wherein said arene containing an OH substituent or an SH substituent corresponds to the formula (III)

Rₙ—Ar—AH     (III)

wherein:
Ar is a monocyclic or bicyclic ring system;
A is sulfur or oxygen;
R is at least one moiety selected from the group consisting of hydrogen, halogen, alkyl, alkoxy, alkylthio, phenoxy, nitro, haloalkyl, alkoxycarbonyl, haloalkoxy, haloalkylthio, phenyl, benzoyl and cyano; and
n is an integer from 1 to 5.

3. The process of claim 2, wherein in the formula (III) n is 1 or 2.

4. The process of claim 1, wherein in the formula (I), R' is a moiety selected from the group consisting of paratoluenesulfonyl and trichloromethanesulfonyl.

5. The process of claim 1, wherein the base is selected from the group consisting of alkali metal hydroxides and carbonates and alkaline earth metal hydroxides and carbonates.

6. The process of claim 1, wherein in the formula (II), R₁, R₂, R₃ and R₄ are selected from the group consisting of a hydrogen atom and a methyl moiety.

7. The process of claim 1, wherein in the formula (II), n is an integer from 0 to 6.

8. The process of claim 1, wherein in the formula (II), R₅ is an alkyl moiety having from 1 to 4 carbon atoms.

9. The process of claim 1, wherein in the formula (II), R₁, R₂, R₃ and R₄ are selected from the group consisting of a hydrogen atom and a methyl moiety, n is an integer from 0 to 6 and R₅ is an alkyl moiety having from 1 to 4 carbon atoms.

10. The process of claim 9, wherein the sequestering agent of formula (II) is tris(3,6-dioxaheptyl)amine of the formula: N—(CH₂—CH₂—O—CH₂—CH₂—O—CH₃)₃.

11. The process of claim 10, wherein in the formula (I), R' is a moiety selected from the group consisting of paratoluenesulfonyl and trichloromethanesulfonyl.

12. The process of claim 2, wherein in the formula (I), R' is a moiety selected from the group consisting of paratoluenesulfonyl and trichloromethanesulfonyl, wherein the sequestering agent of formula (II) is tris(3,6-dioxaheptyl)amine of the formula: N—(CH₂—CH₂—O—CH₂—CH₂—O—CH₃)₃, wherein R in formula (III) is selected from the group consisting of hydrogen, methyl, methoxy, and chloro wherein the base is sodium hydroxide, wherein n in formula (III) is 1; wherein the reaction is performed in the presence of a 1,2,4-trichlorobenzene solvent, wherein the molar ratio of the compound of formula (III) to the compound of formula (I) is 0.7:1 to 1.2:1, wherein the molar ratio of base to the compound of formula (III) is 0.85:1 to 1:1, wherein the molar ratio of the compound of formula (II) to the compound of formula (III) is 0.04:1 to 0.15:1, wherein the reaction is conducted at a temperature from about 120° C. to 186° C. and wherein the reaction is conducted for a time of from about 2 to 12 hours.

13. The process of claim 1, wherein the reaction is performed in the presence of a solvent other than said arene containing an OH substituent or an SH substituent.

14. The process of claim 13, wherein the solvent other than said arene containing an OH substituent or an SH substituent is an apolar or slightly polar aprotic solvent.

15. The process of claim 1, wherein the mole ratio of said arene containing an OH substituent or an SH substituent to the compound of formula (I) is from about 0.5:1 to 5:1.

16. The process of claim 15, wherein the mole ratio of said arene containing an OH substituent or an SH substituent to the compound of formula (I) is from 0.7:1 to 1.5:1.

17. The process of claim 1, wherein the mole ratio of the base to said arene containing an OH substituent is from about 0.5:1 to 1.1:1.

18. The process of claim 1, wherein the mole ratio of the compound of formula (II) to said arene containing an OH substituent or an SH substituent is from about 0.01:1 to 0.2:1.

19. The process of claim 1, wherein the reaction temperature is from about 80° to 200° C.

20. The process of claim 2, wherein Ar is a monocyclic arene ring system.

21. The process of claim 2, wherein Ar is benzene.

22. A process for preparing a substituted or an unsubstituted trifluoroethoxyarene or a substituted or an unsubstituted trifluoroethylthioarene comprising the step of reacting, for a time sufficient to obtain said trifluoroethoxyarene or trifluoroethylthioarene, a substituted or an unsubstituted arene containing an OH substituent or an SH substituent with a compound of the formula (I):

$$CF_3CH_2OR' \quad (I)$$

wherein R' is a moiety selected from the group consisting of trifluoroacetyl, methanesulfonyl, paratoluenesulfonyl, trichloromethanesulfonyl and chlorosulfonyl, in the presence of a solid strong alkaline base and at least one complexing agent of the formula (II):

$$N-[CHR_1-CHR_2-O-(CHR_3-CHR_4-O)_n-R_5]_3 \quad (II)$$

wherein n is an integer from 0 to 10 (0 is less than or equal to n is less than or equal to 10), $R_1$, $R_2$, $R_3$ and $R_4$, which may be identical or different, are selected from the group consisting of a hydrogen atom and an alkyl moiety having from 1 to 4 carbon atoms, and $R_5$ is selected from the group consisting of an alkyl moiety having from 1 to 12 carbon atoms, a cycloalkyl moiety having from 1 to 12 carbon atoms, a phenyl moiety and a moiety of the formula: $-C_mH_{2m}-C_6H_5$ or $C_mH_{2m+1}-C_6H_4-$ wherein m ranges from 1 to 12, with the proviso that said reaction is conducted in the presence of a halogenated organic solvent.

* * * * *